United States Patent
Cao et al.

(10) Patent No.: US 9,538,974 B2
(45) Date of Patent: Jan. 10, 2017

(54) METHODS AND SYSTEMS FOR CORRECTING TABLE DEFLECTION

(71) Applicants: General Electric Company, Schenectady, NY (US); The University of Notre Dame du Lac, Notre Dame, IN (US)

(72) Inventors: Guangzhi Cao, Madison, WI (US); Jiang Hsieh, Brookfield, WI (US); Jean-Baptiste Thibault, Brookfield, WI (US); Jiahua Fan, New Berlin, WI (US); Ken D. Sauer, South Bend, IN (US)

(73) Assignees: General Electric Company, Schenectady, NY (US); The University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/548,846

(22) Filed: Nov. 20, 2014

(65) Prior Publication Data
US 2016/0143607 A1    May 26, 2016

(51) Int. Cl.
| | |
|---|---|
| *G06K 9/00* | (2006.01) |
| *A61B 6/00* | (2006.01) |
| *A61B 6/02* | (2006.01) |
| *A61B 6/03* | (2006.01) |
| *A61B 6/04* | (2006.01) |
| *G06T 11/00* | (2006.01) |
| *G06T 7/00* | (2006.01) |

(52) U.S. Cl.
CPC .............. *A61B 6/5276* (2013.01); *A61B 6/027* (2013.01); *A61B 6/032* (2013.01); *A61B 6/0407* (2013.01); *G06T 7/0012* (2013.01); *G06T 11/003* (2013.01); *G06T 2207/10081* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,608,776 | A * | 3/1997 | Hsieh | G21K 1/04 378/145 |
| 6,134,292 | A | 10/2000 | Hsieh | |
| 6,438,195 | B1 | 8/2002 | Hsieh | |
| 6,639,965 | B1 | 10/2003 | Hsieh et al. | |
| 6,678,346 | B2 | 1/2004 | Hsieh | |
| 6,778,630 | B2 * | 8/2004 | Silver | G06T 11/005 378/15 |
| 7,242,749 | B2 | 7/2007 | Hsieh et al. | |
| 7,327,822 | B2 | 2/2008 | Sauer et al. | |
| 7,344,306 | B2 | 3/2008 | Hsieh et al. | |
| 7,508,903 | B2 * | 3/2009 | Nishide | A61B 6/06 378/15 |
| 7,532,702 | B2 | 5/2009 | Hsieh et al. | |

(Continued)

*Primary Examiner* — Anand Bhatnagar
(74) *Attorney, Agent, or Firm* — Alleman Hall McCoy Russell & Tuttle LLP

(57) ABSTRACT

Various methods and systems are provided for estimating and compensating for table deflection in reconstructed images. In one embodiment, a method for computed tomography (CT) imaging comprises reconstructing images from data acquired during a helical CT scan where table deflection parameters are estimated and the reconstruction is adjusted based on the table deflection parameters. In this way, images may be reconstructed without artifacts caused by table deflection.

12 Claims, 10 Drawing Sheets

(56) References Cited

U.S. PATENT DOCUMENTS

| | | | |
|---|---|---|---|
| 7,734,079 B2* | 6/2010 | Hsieh | G06T 11/006 359/559 |
| 7,983,462 B2 | 7/2011 | Sauer et al. | |
| 8,086,010 B2* | 12/2011 | Nabatame | G06T 7/0012 378/21 |
| 8,792,965 B2* | 7/2014 | Ning | A61B 6/032 378/37 |
| 2003/0123614 A1* | 7/2003 | Silver | G06T 11/005 378/146 |
| 2006/0039536 A1* | 2/2006 | Nishide | A61B 6/06 378/151 |
| 2007/0116172 A1 | 5/2007 | Hsieh et al. | |
| 2008/0123924 A1* | 5/2008 | Nabatame | G06T 7/0012 382/131 |
| 2008/0317196 A1* | 12/2008 | Imai | A61B 6/405 378/8 |
| 2009/0168952 A1* | 7/2009 | Mori | A61B 6/032 378/15 |
| 2013/0251102 A1* | 9/2013 | Noshi | A61B 6/032 378/20 |
| 2015/0243045 A1* | 8/2015 | Ra | G06T 7/0024 382/131 |

* cited by examiner

METHODS AND SYSTEMS FOR CORRECTING TABLE DEFLECTION

FIELD

Embodiments of the subject matter disclosed herein relate to non-invasive imaging, and more particularly, to table deflection estimation and compensation for medical imaging systems.

BACKGROUND

In computed tomography (CT) imaging system configurations, an x-ray source may project a fan-shaped beam, which is collimated to lie within an x-y plane of a Cartesian coordinate system generally referred to as the imaging plane. The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging pane and around the object to be imaged so that the angle at which the x-ray beam intersects the object constantly changes. A group of x-ray attenuation measurements, i.e., projection data, from the detector array at one gantry angle is referred to as a view. A scan of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to as the filtered back projection technique. This process converts the attenuation measurements from a scan into integers called CT numbers or Hounsfield units, which are used to control the brightness of a corresponding pixel on a display.

To reduce the total scan time required for multiple slices, a helical scan may be performed. To perform a helical scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

BRIEF DESCRIPTION

In one embodiment, a method for computed tomography (CT) imaging comprises reconstructing images from data acquired during a helical CT scan where table deflection parameters are estimated and the reconstruction is adjusted based on the table deflection parameters to compensate for table deflection.

For example, table motion may occur during helical scans where the table is expected to strictly move along the axial of the gantry plane. The undesired motion can be caused by many factors, such as mechanical instability and imperfect alignment. Excessive table motion may cause artifacts in reconstructed images, which can be misleading and affect clinical diagnosis. Thus, in some examples, by reconstructing images based on table deflection parameters, it is possible to at least partially reduce artifacts in the reconstructed image, at least in some situations.

It should be understood that the brief description above is provided to introduce in simplified form a selection of concepts that are further described in the detailed description. It is not meant to identify key or essential features of the claimed subject matter, the scope of which is uniquely defined by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of medical imaging systems. In particular, methods and systems are provided for estimating and compensating for table deflection in a computed tomography (CT) imaging system. Table deflection is one type of table motion where the table sags vertically while traveling into or away from the gantry due to the weight of the patient. Table deflection may be especially common when heavy patients are scanned, and becomes a more severe issue when high table speed is required in helical scans, such as for fast chest scans and helical acquisitions using wide detector aperture.

Figure 1:
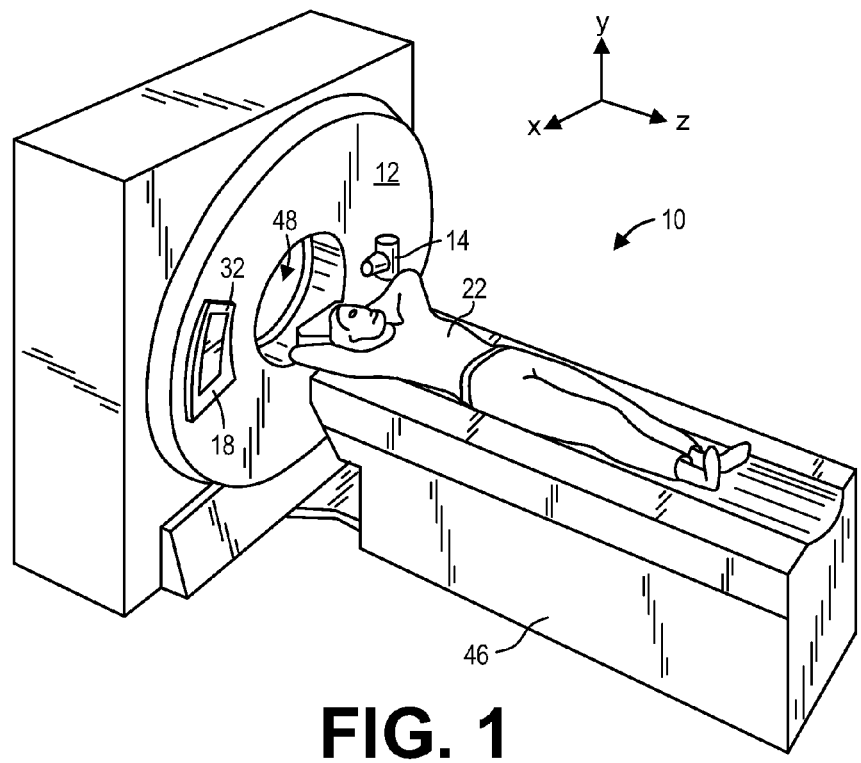
FIG. 1 is a diagrammatical view of a CT system according to an embodiment of the invention.
Figure 2:
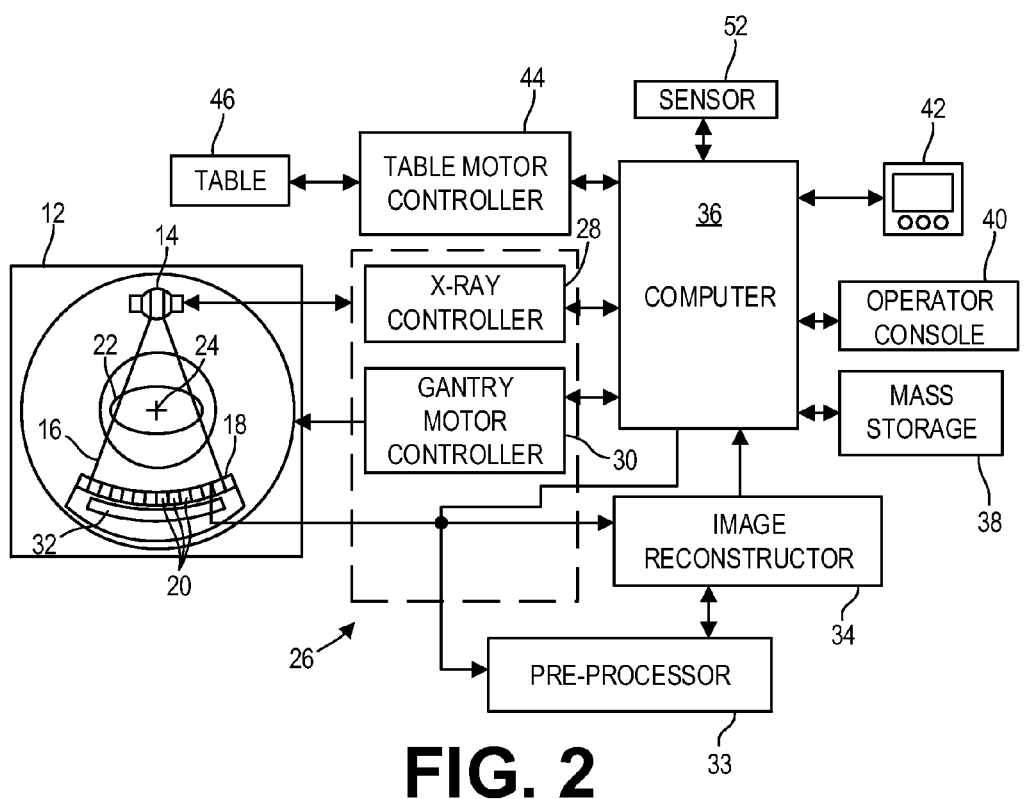
FIG. 2 is a block schematic diagram of an exemplary imaging system according to an embodiment of the invention.

An example of a CT imaging system that may be used to acquire images processed in accordance with the present techniques is provided in FIGS. 1 and 2. Though a CT system is described by way of example, it should be understood that the present techniques may also be useful when applied to images acquired using other imaging modalities, such as tomosynthesis, MRI, PET, SPECT, C-arm angiography, mammography ultrasound, and so forth. The present discussion of a CT imaging modality is provided merely as an example of one suitable imaging modality.

Figure 3:
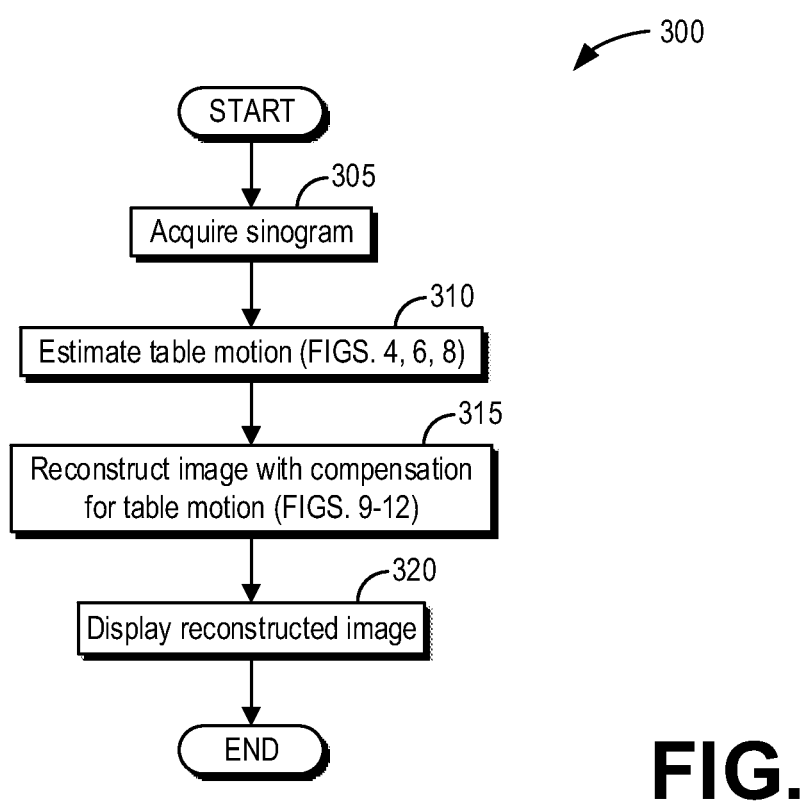
FIG. 3 shows a high-level flow chart illustrating an example method for estimating table motion and compensating for table motion during image reconstruction according to an embodiment of the invention.
Figure 4:
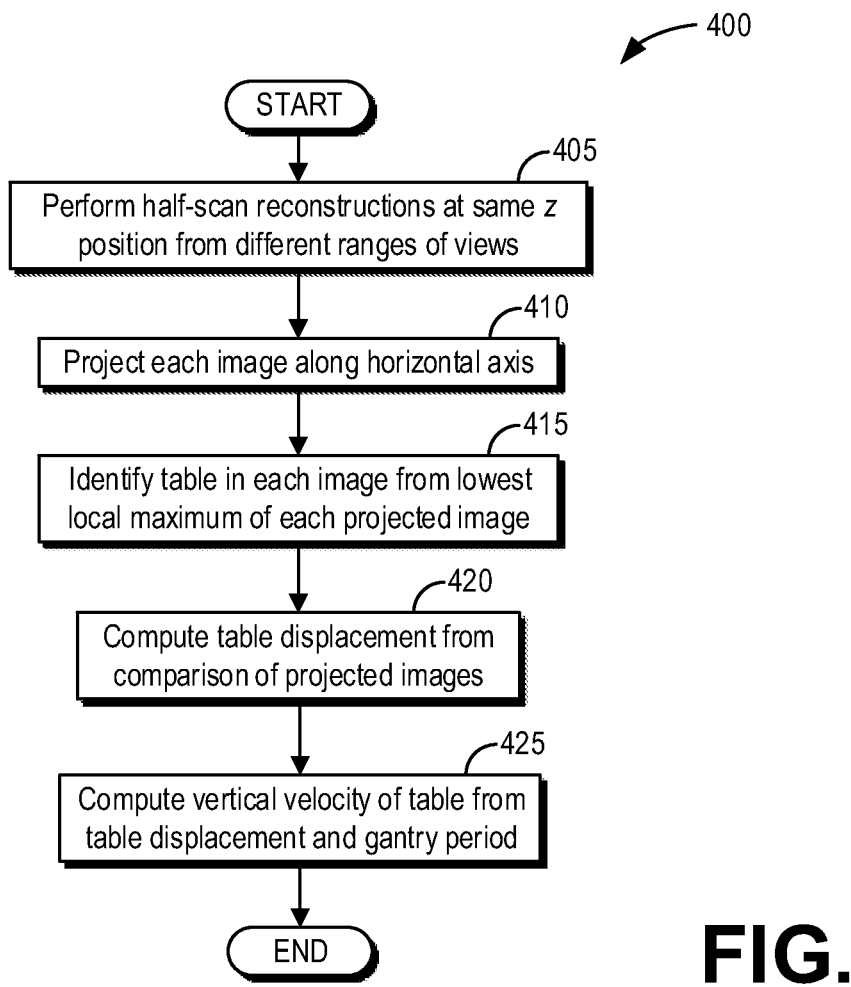
FIG. 4 shows a high-level flow chart illustrating an example method for estimating table deflection using reconstructed image data according to an embodiment of the invention.
Figure 5:
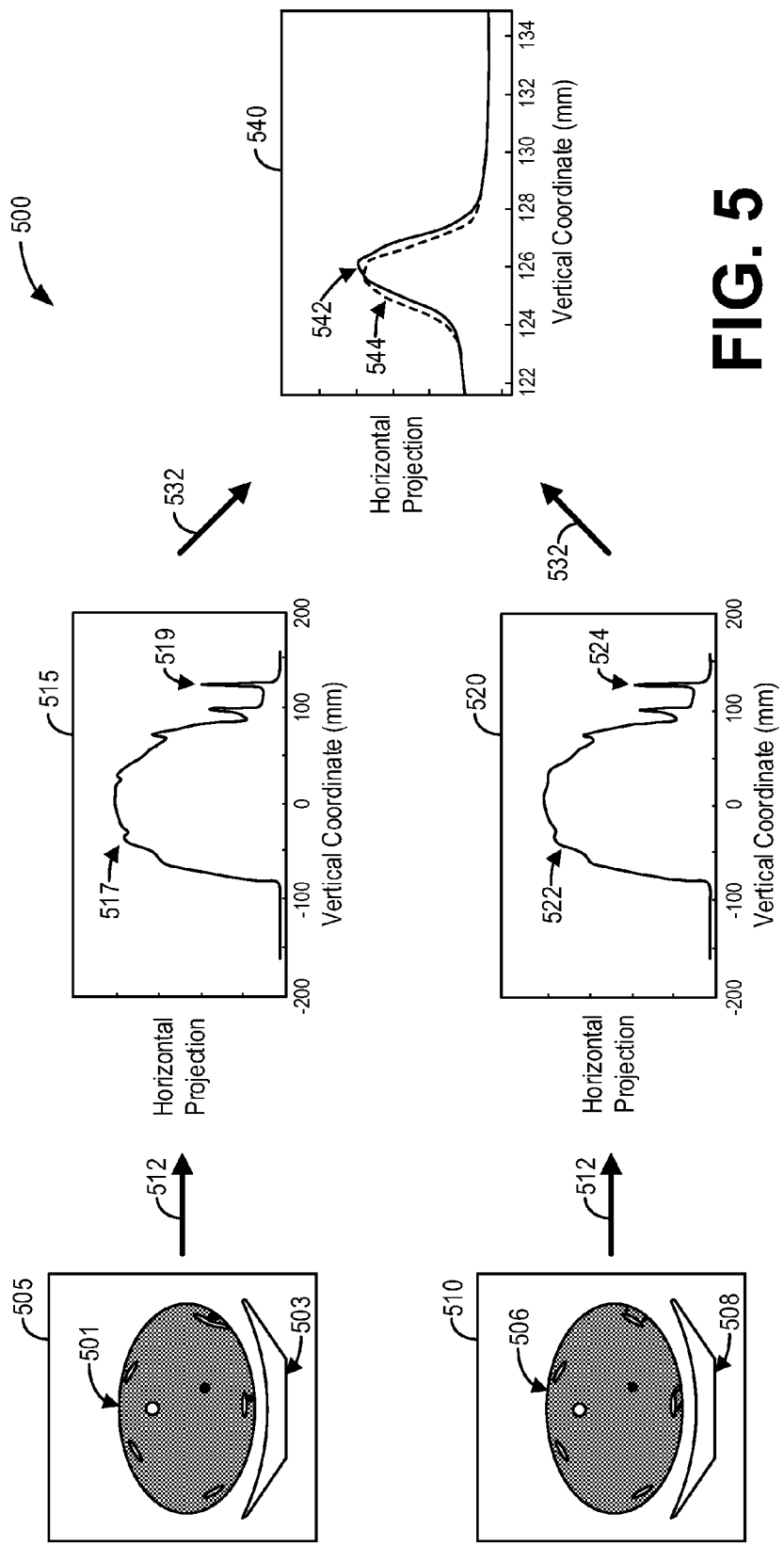
FIG. 5 shows a pictorial overview of estimating table deflection using reconstructed image data according to an embodiment of the invention.
Figure 6:
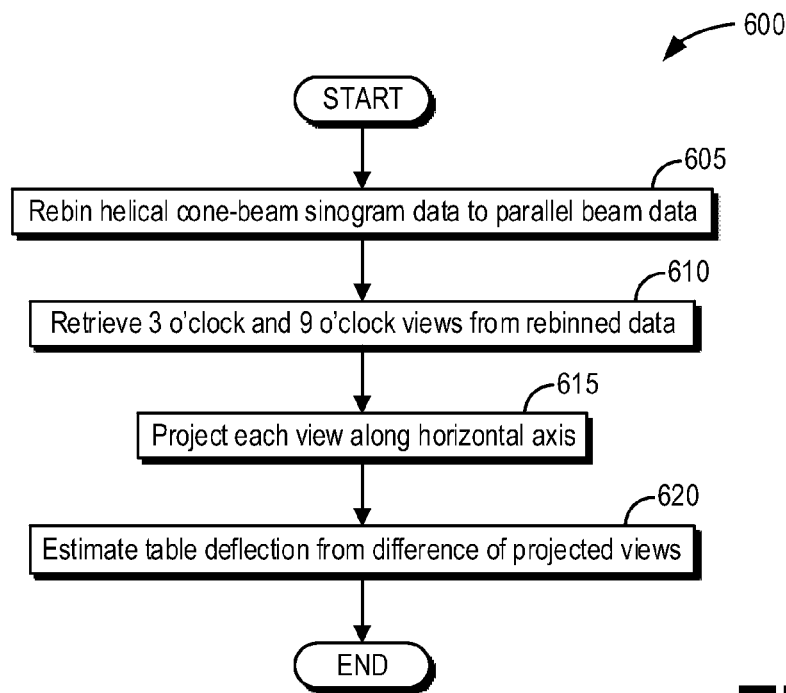
FIG. 6 shows a high-level flow chart illustrating an example method for estimating table deflection using projection data according to an embodiment of the invention.
Figure 7:
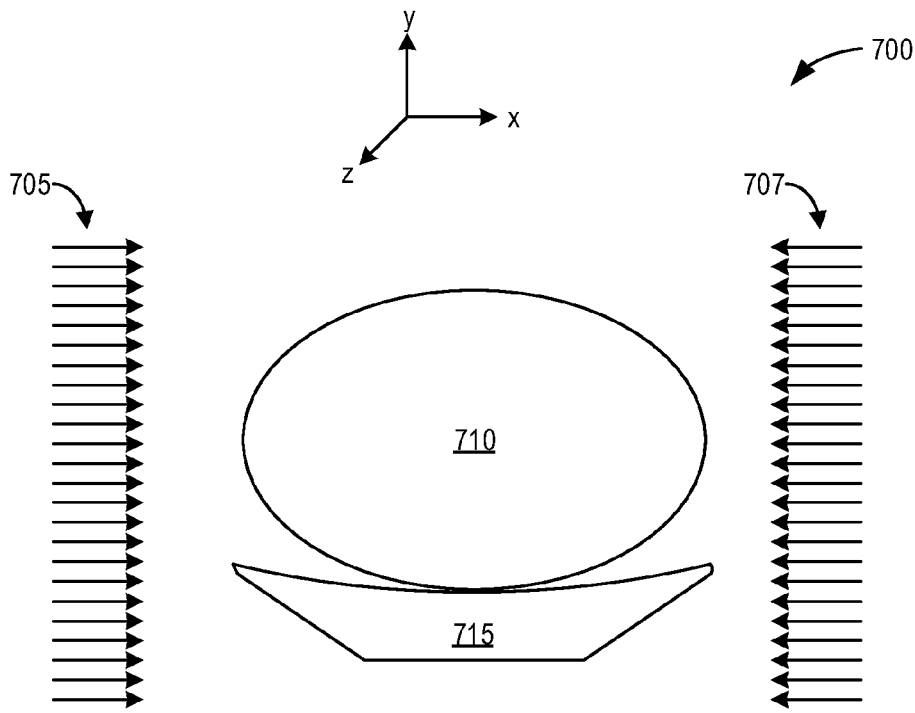
FIG. 7 shows a pictorial overview of estimating table deflection using projection data according to an embodiment of the invention.
Figure 8:
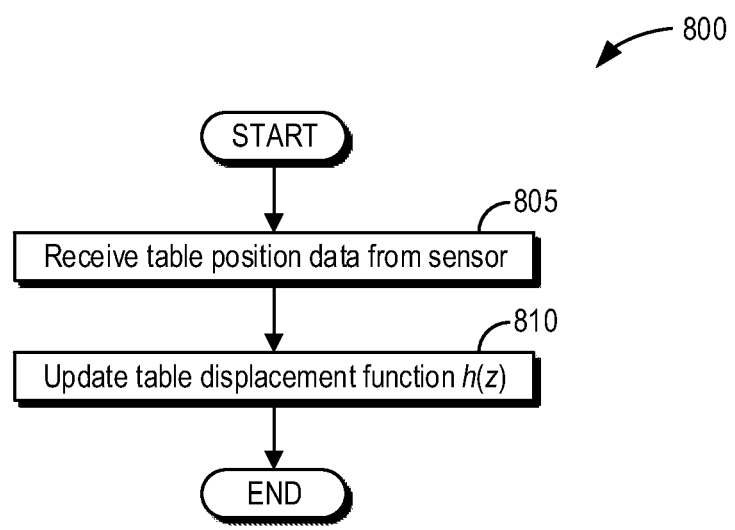
FIG. 8 shows a high-level flow chart illustrating an example method for directly measuring table deflection according to an embodiment of the invention.
Figure 9:
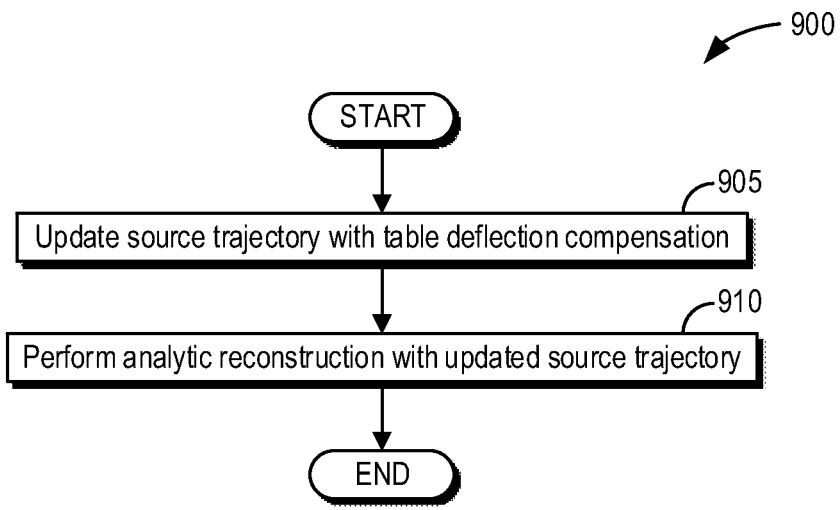
FIG. 9 shows a high-level flow chart illustrating an example method for compensating for table deflection during analytic image reconstruction according to an embodiment of the invention.
Figure 10:
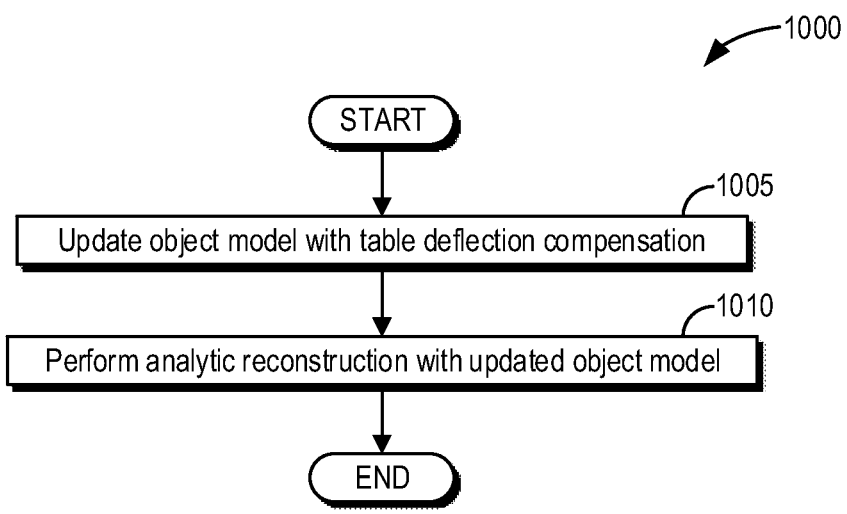
FIG. 10 shows a high-level flow chart illustrating an example method for compensating for table deflection during analytic image reconstruction according to an embodiment of the invention.
Figure 11:
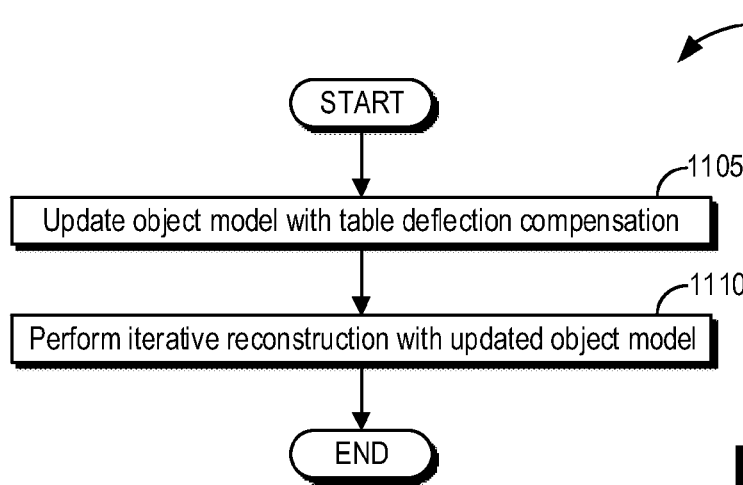
FIG. 11 shows a high-level flow chart illustrating an example method for compensating for table deflection during iterative image reconstruction according to an embodiment of the invention.
Figure 12:
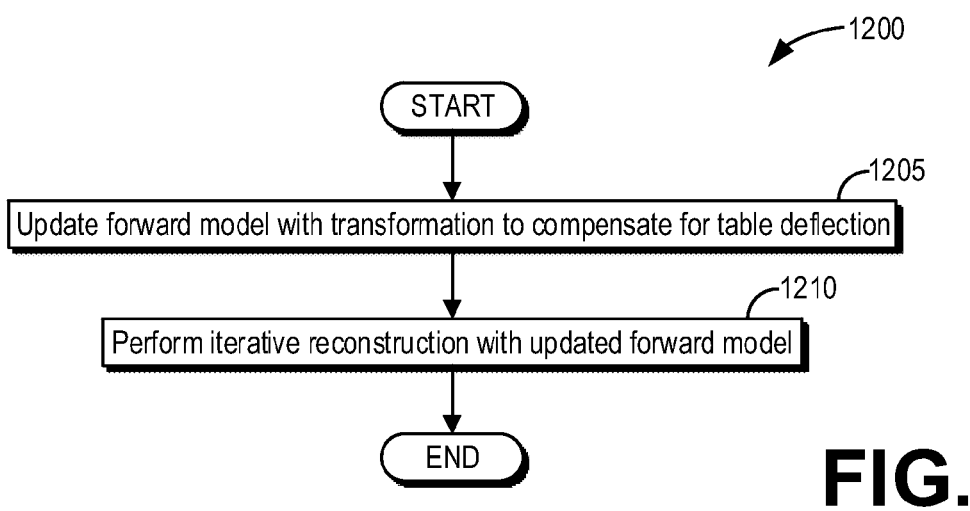
FIG. 12 shows a high-level flow chart illustrating an example method for compensating for table deflection during iterative image reconstruction according to an embodiment of the invention.
Figure 13:
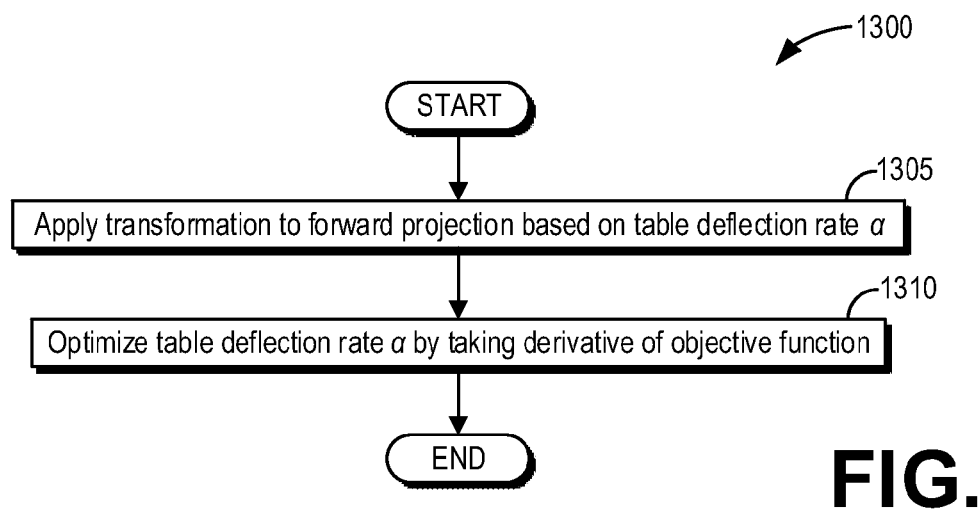
FIG. 13 shows a high-level flow chart illustrating an example method for estimating and compensating for table deflection during iterative image reconstruction according to an embodiment of the invention.
Figure 14:
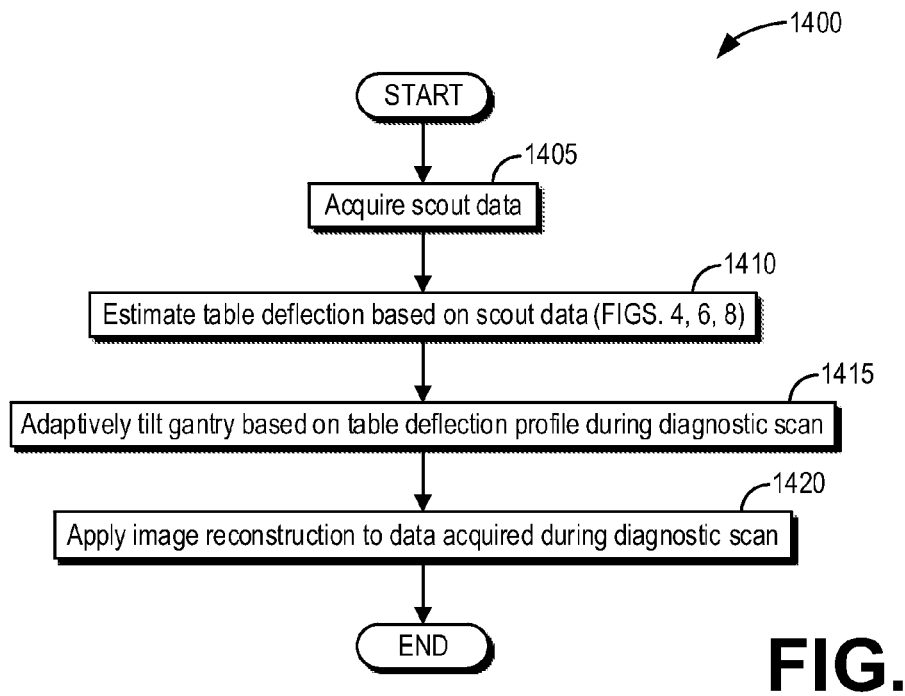
FIG. 14 shows a high-level flow chart illustrating an example method for directly compensating for table deflection during data acquisition according to an embodiment of the invention.
Figure 15:
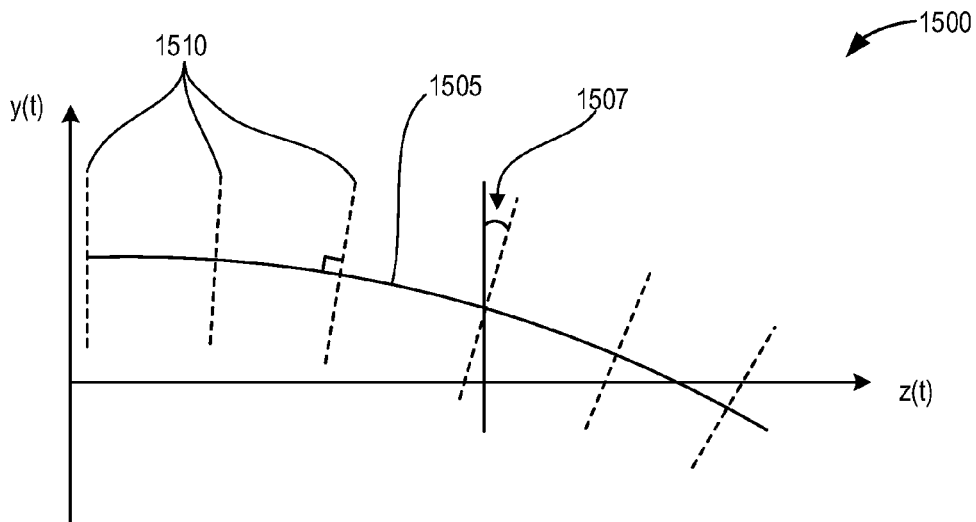
FIG. 15 shows a diagram illustrating an example method for directly compensating for table deflection during data acquisition according to an embodiment of the invention.

The CT system depicted in FIGS. 1 and 2 may be configured to reconstruct images using data acquired during a helical scan. During a helical scan, a table may slide a subject through a gantry while the gantry rotates about the subject and collects CT scan data. The weight of the subject may cause the table to sag, or deflect, during the scan, thereby causing image artifacts in images reconstructed from the scan data. As shown in FIG. 3, a method for correcting such artifacts may include estimating an amount of table deflection and compensating for the table deflection during image reconstruction. Various approaches for determining an amount of table deflection are provided. As shown in FIGS. 4 and 5, the table deflection may be estimated from half-scan reconstructions at the same table position from different views. As shown in FIGS. 6 and 7, the table deflection may be estimated directly from raw projection data by rebinning the helical CT scan data to parallel beam data. As shown in FIG. 8, the table deflection may be directly measured using one or more sensors. After the table deflection is determined, the deflection may be compensated in various ways depending on the algorithm used to reconstruct the images. FIGS. 9 and 10 depict various methods for taking table deflection into account during analytic image reconstruction, while FIGS. 11 and 12 depict various methods for use during iterative image reconstruction. Iterative image reconstruction is also capable of jointly estimating and compensating for table deflection, as shown in FIG. 13. Table deflection may also be compensated for by tilting the gantry, as shown in FIGS. 14 and 15.

Referring to FIGS. 1 and 2, a CT imaging system 10 is shown as including a gantry 12. CT system 10 is a "third generation" CT system. In an alternative embodiment, CT system 10 may be an energy integrating, a photon counting (PC), or a photon energy discriminating (ED) CT detector system. Gantry 12 includes an x-ray source 14 that projects a beam of x-rays 16 toward detector array 18. The x-rays pass through a subject 22, such as a patient, to generate attenuated x-rays. In an alternative embodiment, each detector element 20 of detector array 18 may be a photon energy integrating detector, a photon counting detector, or a photon energy discriminating detector. Each detector element 20 produces an electrical signal that represents an intensity of the attenuated x-rays. During a scan to acquire projection data, gantry 12 and components mounted on gantry 12 rotate about a center of rotation 24.

Rotation of a gantry 12 and an operation of x-ray source 14 are governed by a control mechanism 26 of CT system 10. Control mechanism 26 includes an x-ray controller 28 that provides power and timing signals to x-ray source 14, and a gantry motor controller 30 that controls a rotational speed and position of gantry 12. In some embodiments, gantry motor controller 30 may control a tilt angle of gantry 12. A data acquisition system (DAS) 32 in control mechanism 26 samples and digitizes the projection data from detector elements 20 and converts the projection data to sampled and digitized projection data for subsequent processing. In some embodiments, DAS 32 may be positioned adjacent to detector array 18 on gantry 12, such as depicted in FIG. 2.

Pre-processor 33 receives the sampled and digitized projection data from DAS 32 to pre-process the sampled and digitized projection data. In one embodiment, pre-processing includes, but is not limited to, an offset correction, a primary speed correction, a reference channel correction, an air-calibration, and/or applying a negative logarithmic operation. As used herein, the term processor is not limited to just those integrated circuits referred to in the art as a processor, but broadly refers to a controller, a microcontroller, a microcomputer, a programmable logic controller, an application specific integrated circuit, and any other programmable circuit, and these terms are used interchangeably herein. Pre-processor 33 pre-processes the sampled and digitized projection data to generate pre-processed projection data.

An image reconstructor 34 receives the pre-processed projection data from pre-processor 33 and performs image reconstruction, such as filtered back-projection (FBP), to generate a reconstructed image. The reconstructed image is applied as an input to a computer 36 which stores the reconstructed image in a mass storage device 38, where the mass storage device 38 may include, as non-limiting examples, a hard disk drive, a floppy disk drive, a compact disk-read/write (CD-R/W) drive, a Digital Versatile Disc (DVD) drive, a flash drive, and/or a solid-state storage device. As used herein, the term computer is not limited to just those integrated circuits referred to in the art as a computer, but broadly refers to a processor, a microcontroller, a microcomputer, a programmable logic controller, an application specific integrated circuit, and any other programmable circuit, and these terms are used interchangeably herein. An x-ray controller 28 adjusts a tube current within x-ray source 14 based on a quality of the reconstructed image.

Computer 36 also receives commands and scanning parameters from a user, such as an operator, via a console 40 that includes a user interface device, such as a keyboard, mouse, voice-activated controller, or any other suitable input apparatus. An associated display 42 allows a user, such as an operator, to observe the reconstructed image and other data from computer 36. The commands and scanning parameters are used by computer 36 to provide control signals and information to DAS 32, x-ray controller 28, and gantry motor controller 30. In addition, computer 36 operates a table motor controller 44 which controls a motorized table 46 to position subject 22 within gantry 12. Particularly, table motor controller 44 adjusts table 46 to move portions of subject 22 and center the subject 22 in a gantry opening 48.

In an alternative embodiment, a high frequency electromagnetic energy projection source configured to project high frequency electromagnetic energy toward subject 22 may be used instead of x-ray source 14. A detector array disposed within a gantry and configured to detect the high frequency electromagnetic energy may also be used instead of detector array 18.

In one embodiment, the image reconstructor 34 stores the reconstructed images in the mass storage device 38. Alternatively, the image reconstructor 34 transmits the reconstructed images to the computer 36 for generating useful patient information for diagnosis and evaluation. In certain embodiments, the computer 36 transmits the reconstructed images and/or the patient information to a display 42 communicatively coupled to the computer 36 and/or the image reconstructor 34.

In one embodiment, the display 42 allows the operator to evaluate the imaged anatomy. The display 42 may also allow the operator to select a volume of interest (VOI) and/or request patient information, for example, via graphical user interface (GUI) for a subsequent scan or processing.

In one embodiment, a sensor 52 may track the position of the table 46 during data acquisition. For example, sensor 52 may sense the position of the table 46 with regard to the x, y, and z axes. As such, sensor 52 may comprise one or more sensors positioned on the gantry 12. As another example, sensor 52 may comprise a range sensor positioned on the gantry 12 below the table 46 and configured to sense a distance of the table 46 from the sensor 52. Sensor 52 may communicate a sensed position of the table 46 to the computer 36, the pre-processor 33, and/or the image reconstructor 34. The sensed position of the table 46 during a scan may subsequently be used to compensate for table deflection, as described further herein with regard to FIG. 8.

In one embodiment, CT system 10 may be configured to perform helical scans where the table 46 moves along the axial of the gantry plane (depicted in FIG. 1 and referred to hereinafter as the z-axis) while the gantry 12 rotates the x-ray source 14 and detector 18 in the imaging plane (depicted in FIG. 1 and referred to hereinafter as the x-y plane). During such a helical scan, the table 46 is typically considered and expected to be strictly aligned along the z-axis with zero deflection in the y direction. However, in practice undesirable table motion may occur during a helical scan. Such motion may be caused by factors including but not limited to mechanical instability and imperfect alignment. Excessive table motion may cause significant artifacts in reconstructed images, which can be misleading and affect clinical diagnosis. Table deflection is one type of table motion where the table 46 sags vertically (i.e., along the y-axis) while traveling into or away from the gantry 12 due to the weight of the subject 22. Table deflection is especially common when heavy patients are scanned, and becomes a more severe issue when high table speed is commanded in helical scans, such as for fast chest scans and helical acquisitions using wide detector aperture.

In one embodiment, table deflection may be modeled as a vertical movement with a simple function in a short (i.e., sub-second) time period, for example using approximately linear or quadratic vertical displacement as a function of time. A table motion vector may be estimated for each image slice in real time by calculating the displacement of the same table location in two or more images that have a small time difference. Once the motion vector is obtained, error compensation may be performed during image reconstruction by adding a series of vertical offsets to the modeled gantry position or reconstruction plane in each projection view to account for table deflection.

While the systems and methods provided herein mitigate the motion caused by table deflection, it should be appreciated that the systems and methods may be generalized to address other types of table motion or data inconsistencies as well, such as motion caused by table or gantry misalignments in other dimensions.

It should be appreciated that the methods provided herein overcome a variety of problems specific to helical scans. For example, in axial scans, the problem caused by table deflection and misalignment is image mis-registration between different slabs and the images within each slab are consistent. However, in helical scans the problem is motion artifacts in the images due to modeling inaccuracies from view to view, not from slab to slab as in axial scans, although the images may still be well registered (i.e., the image and the table may still appear exactly aligned among the images). Furthermore, in axial scans, the known table displacement between two boundary slices of neighboring slabs may be used to solve the mis-registration problem. However, in helical scans there is no concept of boundary slices. Instead, all the slices are similarly sampled. Further still, for correction of the potential mis-registration in axial scans, images may simply be shifted along the y axis between slabs. However, as described further herein, for correction of the resulting motion artifacts in helical scans, every view may be shifted appropriately during reconstruction.

FIG. 3 shows a high-level flow chart illustrating an example method 300 for estimating table motion and compensating for table motion during image reconstruction according to an embodiment of the invention. In particular, method 300 relates to estimating a table deflection during a helical CT scan and accounting for the table deflection during image reconstruction. Method 300 may be described with regard to the components and systems depicted in FIGS. 1 and 2, however it should be appreciated that the method may be applied to other systems without departing from the scope of the present disclosure. Method 300 may be carried out by pre-processor 33, image reconstructor 34, and/or computer 36, and may be stored as executable instructions in non-transitory memory of mass storage 38.

Method 300 may begin at 305. At 305, method 300 may include acquiring a sinogram, or raw projection data. The sinogram may be acquired using helical CT wherein the table 46 moves along the z-axis through the gantry 12 at a selected speed while the gantry 12 rotates the detector 18 and x-ray source 14 at a selected rotational speed. Cone beam or fan beam data acquisition systems and methods may be utilized.

At 310, method 300 may include estimating table motion. Estimating table motion may comprise determining a table motion vector. In particular, table deflection may be modeled as a vertical movement with a simple function in a short (i.e., sub-second) time period, for example using approximately linear or quadratic vertical displacement as a function of time. A table motion vector may be estimated for each image slice in real time by calculating the displacement of the same table location in two or more images that have a small time difference.

In one embodiment, estimating table motion may comprise calculating table deflection from image data, or image reconstructions of the helical CT scan data. In one example, table deflection may be estimated from two or more half-scan reconstructions at the same z location. A difference in the table position between images may be used to estimate the table deflection. In another example, table deflection may be estimated from image reconstructions performed at different z locations. Calculating table deflection using image data is described further herein and with regard to FIG. 4.

In another embodiment, estimating table motion may comprise calculating table deflection from projection data, or the raw helical CT scan data. Calculating table deflection using projection data is described further herein and with regard to FIG. 6.

In another embodiment, estimating table motion may comprise directly measuring table deflection using sensors. For example, sensor 52 may sense a precise vertical position of the table 46 for all z positions of the table 46. Directly measuring table deflection using sensors is described further herein and with regard to FIG. 8.

At 315, method 300 may include reconstructing the image while compensating for the table motion estimated at 310. In particular, once the table motion vector is obtained, error compensation may be performed during image reconstruction by adding a series of vertical offsets to the modeled gantry position or reconstruction plane in each projection view to account for table deflection. In this way, image artifacts caused by table deflection may be corrected in reconstructed images.

In one embodiment, the image may be reconstructed form the raw helical CT scan data using an analytic image reconstruction algorithm. For example, the image may be reconstructed using a filtered back-projection (FBP) algorithm, a Feldkamp-Davis-Kress (FDK)-type algorithm, a Katsevich-type algorithm, or other image reconstruction algorithms. Methods for compensating for table deflection during analytic image reconstruction are described further herein and with regard to FIGS. 9 and 10.

In another embodiment, the image may be reconstructed from the raw helical CT scan data using an iterative image reconstruction algorithm. Methods for table deflection compensation during iterative image reconstruction are described further herein and with regard to FIGS. 11 and 12.

At 320, method 300 may include displaying the reconstructed image. The reconstructed image may be displayed on display 42, for example. The reconstructed image may include a reduced number of artifacts caused by table deflection, and thereby may feature an improved image quality compared to images reconstructed without compensating for table deflection. Method 300 may then end.

FIG. 4 shows a high-level flow chart illustrating an example method 400 for compensating table deflection using reconstructed image data according to an embodiment of the invention. Method 400 may be described with regard to the components and systems depicted in FIGS. 1 and 2, however it should be appreciated that the method may be applied to other systems without departing from the scope of the present disclosure.

Method 400 may begin at 405. At 405, method 400 may include performing half-scan reconstructions at the same z position from different ranges of views. For example, for a given slice, method 400 may include performing two half-scan reconstructions at the same z position from different ranges of views. For example, one of the half-scan images may use a center view located near the 3 o'clock position, while the other half-scan image may use a center view near the 9 o'clock position. Therefore, these two reconstructions have a time difference of half of the gantry rotation period.

The two images are reconstructed at the same z location using a different z-offset relative to the center view of each of the two selected view ranges, so that the difference between the two reconstructed images is mostly due to temporal inconsistencies in the input data stream. Using a half-scan reconstruction with FBP makes it possible to minimize the temporal difference between the two images while keeping the images at a consistent z position. Alternatively, more or fewer views per image may be used, in combination with different reconstruction techniques, either analytical or iterative in nature, for flexibility in generating good images from different sets of projection views.

At 410, method 400 may include projecting each reconstructed image along the horizontal axis. Once the two images supported by different ranges of views are available at the same z position, each image may be projected along the horizontal direction (i.e., the x-axis) to identify potential differences in the table position in y seen in each image.

Note that depending on the cone angle of the x-ray beam, helical pitch, and the reconstruction algorithm used, the half-scan reconstructions may contain a certain level of cone beam artifacts. However, since the table supporting the subject's weight changes position very gradually along the z-axis as the scan progresses, the table may be generally well reconstructed.

At 415, method 400 may include identifying the table in each image from the lowest local maximum of each projected image. In the horizontal projections, the lower plate of the table, which is typically horizontal, may be easily localized at the lowest local maximum. Since the cross-section of the table is known, method 400 may also include performing a fitting of the table profile to the reconstructed image to improve robustness. In cases where the table is not fully visible in the image, for example if the table is either fully or partially out of the scan field of view, method 400 may include tracking the difference in observed object boundaries between the two images to determine the amount of shift, since the two images are at the same z location.

At 420, method 400 may include computing a table displacement from a comparison of the projected image. Once the lower plate of the table is localized, the displacement of the table between the two half-scan reconstructions may be calculated using local correlation of the two projected table profiles. The estimated table displacement may be denoted as d.

At 425, method 400 may include computing a vertical velocity of the table from the table displacement and gantry period. Dividing the table displacement d by half of the gantry rotation period leads to the vertical velocity of table deflection at the given slice. Method 400 may then end.

While two half-scan reconstructions are discussed herein above, in some examples where computation time is not a concern, the table deflection may be estimated with more than two half-scan reconstructions. For example, four half-scan reconstructions may be used for estimating table deflection. Four location values $y_1$, $y_2$, $y_3$, and $y_4$ for the table lower plate may be obtained from the four half-scan reconstructions. The table deflection may then be estimated using a higher order fit (e.g., second order or higher), thereby providing an estimate of the table deflection as a function of z, or $h(z)$, in contrast with the simple linear model of constant velocity as described herein above.

As described herein above, one or more pairs of images may be used to estimate table deflection, with each pair comprising two images reconstructed at the same z location from different sets of views. However, in one embodiment, the table deflection may be estimated for each view of the acquired projection data at different z positions. For example, reconstructions (e.g., half-scan, full scan, or any view data set supporting appropriate image results) from any adequate reconstruction algorithm (FBP, FDK, iterative reconstruction, etc.) may generate images at different z positions along the scan trajectory path. In this case, the scanned object boundaries are not to be used to estimate table deflection since the object is expected to change along z. However, the table is expected to remain consistent along z, and the table position in y, for example, may be tracked from image location to image location, using segmentation or one of the techniques above such as the projection of the image along the x-axis to determine the y position of the flat part of the table. By equating each image z position with the x-ray source location, and therefore projection view position, this technique yields an estimate of table positions y at discrete z samples. Using interpolation or a polynomial fit assuming a certain type of table motion (e.g., linear, quadratic, etc.) from sample to sample, a continuous model h(z) may be generated to estimate the table deflection from view to view. With this approach, pre-existing reconstructed images, such as the initial image conditions needed for iterative reconstruction, may be used to estimate table deflection. In this way, table deflection may be accurately estimated at various z positions without performing reconstruction computations specifically for the purpose of table deflection estimation.

In all image-based approaches, it is important that the images be reconstructed at a high enough spatial resolution (i.e., small pixel size) to provide the necessary accuracy for the estimation of the table movement.

FIG. 5 shows a pictorial overview 500 of estimating table deflection using reconstructed image data according to an embodiment of the invention. In particular, overview 500 illustrates how table deflection may be measured from two half-scan reconstructions taken at the same z position as described herein above with regard to FIG. 4.

Overview 500 includes two half-scan reconstructed images 505 and 510 reconstructed from the same z position and different views. For example, the first half-scan reconstruction 505 may be reconstructed from a 3 o'clock view, while the second half-scan reconstruction 510 may be reconstructed from a 9 o'clock view. Each image may comprise a reconstructed image of the same subject 22 and the same table 46. In particular, the first half-scan reconstruction 505 may comprise a reconstructed image of the subject 501 and the table 503, while the second half-scan reconstruction 510 may comprise a reconstructed image of the subject 506 and the table 508.

Each image may be projected 512 along the horizontal (x) axis. The graph 515 comprises a plot 517 of the horizontal projection of image 505 as a function of vertical coordinate. The lowest local maximum 519 represents the bottom, flat part of the table 503. The graph 520 comprises a plot 522 of the horizontal projection of image 510 as a function of vertical coordinate. The lowest local maximum 524 represents the bottom, flat part of the table 508.

The peaks representing the flat part of the table in each image may be correlated 532 to compare the vertical positions of the table in each image. The graph 540 comprises plots 542 and 544 of the lowest local maximums 522 and 524, respectively. The table deflection d at the specified z position comprises the difference in vertical coordinate between plot 542 and plot 544. In the example depicted, the table deflection is d=0.38 mm during half of the gantry rotation period. As the views represented by image 505 and image 510 are temporally separated by half of the gantry period, dividing the table deflection d by half of the gantry period yields the table deflection rate. Given the table deflection rate and the estimated deflection d at the position z, the table deflection may be estimated at any position z by assuming the table deflection rate is constant.

FIG. 6 shows a high-level flow chart illustrating an example method 600 for estimating table deflection using projection data according to an embodiment of the invention. Estimating potential table deflection, as a y shift for example, from view to view directly from the projection data is a challenging task. At arbitrary projection angles, the table profile is superposed with the object profile. In addition, the fan-beam or cone-beam nature of the x-ray beam adds other difficulties due to magnification effects. Method 600 thus relates to rebinning projection data and tracking the table profile to obtain an estimation of table deflection. Method 600 may be described with regard to the components and systems depicted in FIGS. 1 and 2, however it should be appreciated that the method may be applied to other systems without departing from the scope of the present disclosure.

Method 600 may begin at 605. At 605, method 600 may include rebinning the helical native cone-beam sinogram data to parallel beam data in the x-y plane (i.e., the gantry plane). Starting from helical cone-beam sinogram data, composed of a single projection view at each table z location, a rebinning operation from cone-beam to parallel-beam is conducted. This eliminates the difficulty of dealing with system magnification by re-sampling the data along an inverted cone geometry with parallel rays in the plane of the gantry while retaining the cone shape along the z-axis for the detector rows. It should be appreciated that the method described herein is not limited to cone-beam sinogram data. For example, in some embodiments, the raw helical CT scan data may comprise helical fan-beam sinogram data. In such examples, method 600 may include rebinning the helical fan-beam sinogram data to parallel beam data in the x-y plane.

Continuing at 610, method 600 may include retrieving 3 o'clock and 9 o'clock views from the rebinned data. For example, as depicted by the pictorial overview 700 in FIG. 7, the 3 o'clock view 705 and the 9 o'clock view 707 may be retrieved from the rebinned parallel beam projection data. Each view 705 and 707 may include projection data regarding the same subject 710 and table 715 separated by half a gantry rotation. The 3 o'clock view 705 and the 9 o'clock view 707 may then be compared to estimate the amount of table deflection in half a gantry rotation.

A similar motion estimation approach as described herein above may be utilized. For example, at 615, method 600 may include projecting each view along the horizontal axis as described herein above with regard to FIGS. 4 and 5. At 620, method 600 may include estimating table deflection from a difference of the projected views. Method 600 may then end.

Although method 600 may be more computationally efficient than image-based methods such as method 400, method 600 may provide less temporal accuracy as the method is limited to a half rotation. Furthermore, the accuracy may be affected by resolution loss in the rebinning operation. Further still, method 600 may be difficult to generalize to higher order motion models and other motion types such as table misalignment.

In another embodiment, scout scans are acquired for positioning or other reasons prior to the diagnostic scan for which an estimation of table deflection is desired. Since the scout scan yields a projection data stream (also used directly as an image after processing), this proposed estimation method also counts as a projection-based method. As long as the scout and diagnostic scans are well registered, table location estimation from the scout may be used for the reconstruction of the diagnostic scan. If table deflection is insensitive to table speed and generally repeatable, the lateral scout images may be used for determining the table y position at each z position as well. A similar motion estimation approach as described herein above may be utilized. Table estimation may, for example, be easily performed from the lateral scout, providing the table deflection function h(z) directly by tracking a fixed point on the projection of the table from view to view.

FIG. 8 shows a high-level flow chart illustrating an example method 800 for directly measuring table deflection according to an embodiment of the invention. In particular, method 800 relates to sensor-based detection of table deflection. Method 800 may be described with regard to the components and systems depicted in FIGS. 1 and 2, however it should be appreciated that the method may be applied to other systems without departing from the scope of the present disclosure.

Method 800 may begin at 805. At 805, method 800 may include receiving table position data from a sensor. For example, the table may be equipped with one or more sensors 52 to provide a continuous stream of z, y, and in some examples x positions of the table for each triggered view. The positions may be saved, for example, with the view data stream for later use during reconstruction. As another example, a range sensor 52 may be mounted at the bottom of the gantry opening to detect the distance to the bottom of the table 46.

At 810, method 800 may include updating a table displacement function h(z). The table displacement function h(z) may comprise the measured vertical position (i.e., y) of the table at each z position. Method 800 may then end.

In this way, additional hardware and electronics in the CT system 10 provides direct measurement, thereby increasing accuracy and eliminating a reliance on the estimation methods described herein above.

After estimating or directly measuring the table displacement and creating a table displacement function h(z), for example using the methods described herein above, the CT system 10 may utilize the table displacement function to compensate for the table deflection during image reconstruction. In some examples, the compensation may be applied as a series of vertical offsets to the modeled gantry position or reconstruction plane in each projection view. For example, in analytical image reconstruction, it is equivalent to compensate for table deflection either from the point of view of a modified x-ray source trajectory or from the point of view of a dynamic object during the acquisition. A method for compensating for table deflection from the point of view of a modified x-ray source is described further herein with regard to FIG. 9, while a method for compensating for table deflection from the point of view of a dynamic object is described further herein with regard to FIG. 10.

FIG. 9 shows a high-level flow chart illustrating an example method 900 for compensating for table deflection during analytic image reconstruction according to an embodiment of the invention. In particular, method 900 relates to modifying an x-ray source to compensate for table deflection during analytic image reconstruction. Method 900 may be described with regard to the components and systems depicted in FIGS. 1 and 2, however it should be appreciated that the method may be applied to other systems without departing from the scope of the present disclosure.

Method 900 may begin at 905. At 905, method 900 may include updating a source trajectory with a table deflection compensation factor. Specifically, from the point of view of a modified source trajectory, the scan helix may be viewed as gradually shifting along the y-axis, for instance. The conventional helical source trajectory in a three-dimensional space is given by $$ST(\beta) = \left(R\sin\beta, R\cos\beta, \frac{H}{2\pi}\beta\right), \beta \subseteq [\beta_s, \beta_e],$$

where $\beta_s$ and $\beta_e$ correspond to the starting and end points of the helical source trajectory, respectively, H is the distance traveled by the source focal spot per rotation along the z-axis, and R is the radius of the helical source trajectory. Assuming d is the displacement that is obtained in the table motion estimation, the modified helical source trajectory that takes the table deflection into account is therefore given by $$ST(\beta) = \left(R\sin\beta, R\cos\beta + \frac{d}{\pi}\beta, \frac{H}{2\pi}\beta\right).$$

At 910, method 900 may include performing analytic reconstruction with the updated source trajectory. Analytic reconstruction may be performed using any analytic reconstruction algorithm, for example a FBP algorithm, a FDK algorithm, a Katsevich-type algorithm, and so on. Method 900 may then end.

FIG. 10 shows a high-level flow chart illustrating an example method 1000 for compensating for table deflection during analytic image reconstruction according to an embodiment of the invention. In particular, method 1000 relates to modifying the back-projected image volume to compensate for table deflection. Method 1000 may be described with regard to the components and systems depicted in FIGS. 1 and 2, however it should be appreciated that the method may be applied to other systems without departing from the scope of the present disclosure.

Method 1000 may begin at 1005. At 1005, method 1000 may include updating an object model with a table deflection compensation factor. From the point of view of a dynamic scanned object, the model of the object f(x,y,z) with compensation for table deflection in a helical scan using discrete views may be given by $$\hat{f}(x, y, z) = \frac{\pi}{M} \sum_{i=0}^{M-1} \hat{f}_i(x, y + h(z), z),$$

where M is the number of total views used for reconstructing one slice, h(z) is the estimated table deflection function as a function of table position z, and $\hat{f}_i(x,y,z)$ is the filtered back-projection of view i at slice location z. As mentioned herein above, the function h(z) may be a simple linear model as $$\frac{2d}{N_V}i,$$

where $N_v$ is the number of the total views per rotation using two half-scan reconstructions, or a higher-order function using more than two half-scan reconstructions or another estimation method, which may suggest a trade-off between computation cost and estimation accuracy.

At 1010, method 1000 may include performing analytic reconstruction with the updated object model. Taking the view-weighted FDK-type reconstruction algorithm as a non-limiting, illustrative example, the function may be expressed as $$\hat{f}_i(x, y, z) = \frac{R^2}{L^2(x, y, \beta_i)} w(\alpha, \beta_i, \gamma) \tilde{p}(\alpha, \beta_i, \gamma),$$

$$\tilde{p}(\alpha, \beta_i, \gamma) = \cos\alpha[(\cos\gamma \cdot p(\alpha, \beta_i, \gamma)) \otimes g(\gamma)],$$

$$L(x, y, \beta_i) = \sqrt{(R + x\cos\beta_i + y\sin\beta_i)^2 + (-x\sin\beta_i + y\sin\beta_i)^2}.$$

where $\alpha$, $\beta_i$, $\gamma$ are the cone angle, view angle, and fan angle, respectively, R is the radius of the helical source trajectory, $p(\alpha, \beta_i, \gamma)$ is the projection, $g(\gamma)$ is the one-dimensional ramp filter kernel, $w(\alpha, \beta_i, \gamma)$ is the view weighting function, and $\otimes$ is the one-dimensional convolution operator. Since each view is treated independently of the others during back-projection, a person skilled in the art will recognize that the compensation works regardless of which specific helical reconstruction algorithm is used. For example, it may be the FBP algorithm, a FDK-type algorithm, a Katsevish-type algorithm, or other reconstruction algorithms. Method 1000 may then end.

In iterative reconstruction, the image f is estimated by successively updating the image to find the solution which best matches the acquired data according to a model of the operation of the CT system 10. In model-based iterative reconstruction (MBIR), for example, the image is reconstructed to minimize a cost function such as $$\hat{f} = \underset{f \geq 0}{\mathrm{argmin}} \{G(Af, p) + U(f)\},$$

where $G(Af,p)$ is the data mismatch term that penalizes the differences between the image f and the projection data p according to the forward model with linearized system matrix A such that p=Ax, and $U(f)$ is a regularization function. The function G, referred to in the art as the objective function, typically stems from a statistical model for the distribution of the acquired x-ray counts. A quadratic formulation of the objective function typically yields good results, such as $$G(Af,p) = (p-Af)^T W(p-Af),$$

where W is a diagonal matrix of statistical confidence weights with entries $w_i$ associated with each projection data point $p_i$. In practice, the reconstruction problem formulated above is ill-conditioned due to the high dimension of A and the large difference in the eigenvalues of W, and is therefore typically solved using an iterative approach.

If table deflection occurs during the acquisition but is ignored during iterative reconstruction, inconsistency between the model and the data may create artifacts in the reconstructed images. Artifacts may even be worse than in analytical reconstruction due to the global nature of the optimization process. Thus, several methods for compensating for table deflection during iterative reconstruction are provided herein below.

FIG. 11 shows a high-level flow chart illustrating an example method 1100 for compensating for table deflection during iterative image reconstruction according to an embodiment of the invention. In particular, method 1100 relates to modifying an object model to compensate for table deflection and using the modified object model for iterative image reconstruction. Method 1100 may be described with regard to the components and systems depicted in FIGS. 1 and 2, however it should be appreciated that the method may be applied to other systems without departing from the scope of the present disclosure.

Method 1100 may begin at 1105. At 1105, method 1100 may include updating an object model with a table deflection compensation factor. In particular, the object may be modeled as changing as a function of time (or z position during the helical scan) as described herein above with regard to FIG. 10 based on the prior knowledge of h(z).

At 1110, method 1100 may include performing iterative reconstruction with the updated object model. Iterative reconstruction may be otherwise performed as known and practiced in the art. Method 1100 may then end.

FIG. 12 shows a high-level flow chart illustrating an example method 1200 for compensating for table deflection during iterative image reconstruction according to an embodiment of the invention. In particular, method 1200 relates to modifying a forward model for iterative reconstruction to compensate for table deflection. Method 1200 may be described with regard to the components and systems depicted in FIGS. 1 and 2, however it should be appreciated that the method may be applied to other systems without departing from the scope of the present disclosure.

Method 1200 may begin at 1205. At 1205, method 1200 may include updating a forward model with a transformation to compensate for table deflection. In particular, compensation for table deflection may be built into the forward model as a transformation:

$$\hat{f} = \underset{f \geq 0}{\mathrm{argmin}} \{G(H(Af, p) + U(f)\},$$

or $H(Af)=HAf$ in the linear case. For implementation, each view of the helical scan may be considered to be shifted by $d=h(z)$ along the vertical axis.

At 1210, method 1200 may include performing iterative reconstruction with the updated forward model. Iterative reconstruction may be otherwise performed as known and practiced in the art. Method 1200 may then end.

Iterative reconstruction is also capable of estimating the amount of table deflection directly during reconstruction instead of requiring a separate estimation process as described herein above. FIG. 13 shows a high-level flow chart illustrating an example method 1300 for jointly estimating and compensating for table deflection during iterative image reconstruction according to an embodiment of the invention. Method 1300 may be described with regard to the components and systems depicted in FIGS. 1 and 2, however it should be appreciated that the method may be applied to other systems without departing from the scope of the present disclosure.

Method 1300 may begin at 1305. At 1305, method 1300 may include applying a transformation to a forward projection based on a table deflection rate $\alpha$. For example, suppose the position of the isocenter drops at a rate $d=\alpha z$. Let $\tilde{p}_i(\alpha) = [H_\alpha(Af)]_i$ be the i-th forward projection as a function of the table deflection rate α. In the quadratic case, the log-likelihood term in the objective function is then $$G(\tilde{p}(\alpha), p) = \sum_{i=0}^{M} w_i(p_i - \tilde{p}_i(\alpha))^2.$$

At 1310, method 1300 may include optimizing the table deflection rate α by taking a derivative of the objective function. That is, in order to estimate α, the objective function may be differentiated:

$$\frac{d}{d\alpha}G(\tilde{p}(\alpha), p) = 2\sum_{i=0}^{M} w_i(p_i - \tilde{p}_i(\alpha))\frac{d\tilde{p}_i}{d\alpha},$$

where the derivative may be written as $$\frac{d\tilde{p}_i}{d\alpha} = \frac{d\tilde{p}_i}{dt}\frac{dt}{d\alpha} = z\cos\theta\frac{d\tilde{p}_i}{dt},$$

where θ describes the angle between the imaging plane and the table. The spatial derivative $d\tilde{p}_i/dt$ may be approximated from sinogram entries. For compensation, the center of image slice k may be perturbed by $\hat{\alpha}z_k$, after which $\hat{\alpha}$ may be re-estimated. In this framework, iterative reconstructions offers the option of joint (or successive) estimation of both the table deflection parameters and the reconstructed image, providing potentially better results than initial estimation followed by one-time compensation during reconstruction.

In one embodiment, table deflection may be compensated during reconstruction by proactively adjusting the acquisition to compensate for the amount the table deflects during the scan itself. If the table deflection profile is known ahead of time before the scan is taken, either from a model of the system or using one of the techniques described above based on table instrumentation or characterization from scout data, the CT system 10 may compensate for table deflection by adaptively adjusting the gantry tilt angle during the diagnostic scan in order to keep the plane of the gantry effectively perpendicular to the instantaneous axis of table travel at any point in time.

FIG. 14 shows a high-level flow chart illustrating an example method 1400 for directly compensating for table deflection during data acquisition according to an embodiment of the invention. Method 1400 may be described with regard to the components and systems depicted in FIGS. 1 and 2, however it should be appreciated that the method may be applied to other systems without departing from the scope of the present disclosure.

Method 1400 may begin at 1405. At 1405, method 1400 may include acquiring scout data. At 1410, method 1400 may include estimating table deflection based on scout data. Table deflection may be estimated using any of the methods described herein above. For example, table deflection may be estimated using half-scan reconstructed images as described herein with regard to FIG. 4, or may be estimated using rebinned projection data as described herein with regard to FIG. 6. As another example, table deflection may be directly measured using sensors as described herein with regard to FIG. 8.

At 1415, method 1400 may include adaptively tilting the gantry based on a table deflection profile during a diagnostic scan. In particular, the gantry 12 may be tilted to maintain a right angle between the table and the imaging plane throughout the diagnostic scan.

As an illustrative example, FIG. 15 shows a graph 1500 illustrating how a gantry 12 may be tilted during a diagnostic scan to compensate for table deflection. Plot 1505 depicts an example table trajectory over time during a helical CT scan. As the time (and table position z) increases, the table 46 deflects in the vertical (y) direction, as shown by plot 1505. The dashed lines 1510 represent the instantaneous gantry plane, or imaging plane. At each value of z, the gantry 12 is tilted by a gantry tilt angle 1507 based on the estimated table deflection profile. As a result, the gantry plane 1510 may remain orthogonal to the table trajectory 1505 by adjusting the gantry tilt angle 1507. As such, the tilt angle 1507 may continuously change during a scan. In this way, no further correction is needed during image reconstruction.

Returning to FIG. 14, at 1420, method 1400 may include applying an image reconstruction algorithm to the data acquired during the diagnostic scan. An analytic or iterative image reconstruction algorithm may be applied to the data without any additional modifications to the algorithm, as the table deflection is compensated during data acquisition. Method 1400 may then end.

The technical effect of the disclosure may include the display of a reconstructed image free of image artifacts caused by table deflection. Another technical effect of the disclosure may include the compensation for table deflection during image reconstruction. Yet another technical effect of the disclosure may include the physical tilting of a gantry during a diagnostic scan to compensate for table deflection.

In one embodiment, a method for CT imaging comprises reconstructing images from data acquired during a helical CT scan where table deflection parameters are estimated and the reconstruction is adjusted based on the table deflection parameters.

In one example, the table deflection parameters are estimated from image reconstructions of the helical CT scan data. In some examples, the image reconstructions comprise at least two half-scan reconstructions at a same z location. In other examples, the image reconstructions comprise at least two half-scan reconstructions at different z locations. Estimating the table deflection parameters comprises measuring a difference in a table position between images.

In another example, the table deflection parameters are estimated directly from the helical CT scan data. For example, the helical CT scan data is rebinned to form parallel beam projections, and estimating the table deflection parameters comprises measuring a difference between two of the parallel beam projections.

In another example, the table deflection parameters are obtained from previously acquired scout data. As yet another example, the table deflection parameters are obtained from direct table sensor measurements taken during the helical CT scan.

In one example, a compensation during the reconstruction is performed by shifting a back-projected image volume differently for each acquired projection view according to the table deflection parameters. In another example, a compensation during the reconstruction is performed by shifting each individual acquired projection view differently according to the table deflection parameters.

In yet another example, the table deflection parameters are updated after the reconstruction and fed into another reconstruction with consequently higher accuracy. In some examples, the table deflection parameters are estimated and compensated jointly during a model-based iterative reconstruction.

In another embodiment, a method for helical CT data acquisition comprises adaptively tilting a gantry during a scan based on a table trajectory. In one example, adaptively tilting the gantry comprises tilting the gantry to maintain the gantry orthogonal to the table trajectory. In another example, the table trajectory is estimated based on a scout scan.

In yet another embodiment, an imaging system comprises a table, a source configured to generate energy, a detector configured to detect the energy, and a processor configured to reconstruct images from data acquired from the detector where a deflection of the table is estimated and the reconstruction is adjusted based on the estimated deflection.

In one example, the system further comprises a display, and the processor is further configured to display the reconstructed images on the display.

In another example, the deflection is estimated based on a difference between two half-scan reconstructions comprising different views of a same position of the table. In yet another example, the reconstruction is adjusted by shifting a back-projected image volume differently for each acquired projection view according to the estimated deflection.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for computed tomography (CT) imaging, comprising:
   acquiring projection data during a helical CT scan of a subject;
   reconstructing at least two images by applying an image reconstruction algorithm to the projection data;
   estimating table deflection parameters based on the at least two image reconstructions; and
   reconstructing an image by applying the image reconstruction algorithm to the projection data, wherein the image reconstruction algorithm is modified based on the table deflection parameters to compensate for table deflection.

2. The method of claim 1, wherein the at least two image reconstructions comprise at least two half-scan reconstructions at a same z location and different view angles.

3. The method of claim 1, wherein the at least two image reconstructions comprise at least two half-scan reconstructions at different z locations.

4. The method of claim 1, wherein estimating the table deflection parameters comprises measuring a difference in a table position between the at least two image reconstructions.

5. The method of claim 1, wherein the image reconstruction algorithm is modified by shifting a back-projected image volume differently for each acquired projection view according to the table deflection parameters.

6. The method of claim 1, wherein the image reconstruction algorithm is modified by shifting each individual acquired projection view differently according to the table deflection parameters.

7. An imaging system, comprising:
   a table;
   a source configured to generate energy;
   a detector configured to detect the energy; and
   a processor configured to:
      acquire CT projection data from the detector during a scan of an object placed on the table;
      estimate a deflection of the table directly from the acquired CT projection data; and
      reconstruct CT images from the acquired CT projection data where the reconstruction is adjusted based on the estimated deflection.

8. The system of claim 7, wherein the processor is further configured to rebin the acquired CT projection data to form parallel beam projections, and wherein estimating the deflection of the table comprises measuring a difference between two of the parallel beam projections.

9. The system of claim 7, wherein the deflection of the table is estimated and compensated jointly during the reconstruction, wherein the reconstruction comprises a model-based iterative reconstruction.

10. The system of claim 9, wherein the estimated deflection of the table is updated after the reconstruction and fed into another reconstruction with consequently higher accuracy.

11. The system of claim 7, further comprising a display, and wherein the processor is further configured to display the reconstructed CT images on the display.

12. The system of claim 11, wherein the reconstruction is adjusted by shifting a back-projected image volume differently for each acquired projection view according to the estimated deflection.

* * * * *